United States Patent [19]

Korthoff et al.

[11] Patent Number: 5,156,615
[45] Date of Patent: Oct. 20, 1992

[54] SURGICAL NEEDLE-SUTURE ATTACHMENT FOR CONTROLLED SUTURE RELEASE

[75] Inventors: Herbert W. Korthoff, Westport; Michael S. Kassim, Monroe, both of Conn.

[73] Assignee: United States Surgical Corporation, Norwalk, Conn.

[21] Appl. No.: 794,736

[22] Filed: Nov. 18, 1991

Related U.S. Application Data

[63] Continuation-in-part of Ser. No. 532,961, Jun. 4, 1990, Pat. No. 5,067,959, which is a continuation-in-part of Ser. No. 413,240, Sep. 27, 1989, abandoned.

[51] Int. Cl.$^5$ .............................. A61B 17/00
[52] U.S. Cl. ................... 606/224; 606/227; 606/225
[58] Field of Search .................. 606/222-228

[56] References Cited

U.S. PATENT DOCUMENTS

| | | | |
|---|---|---|---|
| 86,769 | 2/1869 | Marriott | 606/224 |
| 295,612 | 3/1884 | Bailey | 606/224 |
| 299,305 | 5/1884 | Weed | 606/224 |
| 877,476 | 1/1908 | Bach | 606/224 |
| 1,106,667 | 8/1914 | Minahan | 606/224 |
| 1,250,114 | 12/1917 | Bigelow et al. | 606/223 |
| 1,558,037 | 10/1925 | Morton | 606/224 |
| 1,591,021 | 7/1926 | Davis | 606/224 |
| 1,613,206 | 1/1927 | Souttar | 606/224 |
| 1,665,216 | 4/1928 | Morton et al. | 606/224 |
| 1,678,361 | 7/1928 | Shearon | 606/224 |
| 1,757,129 | 5/1930 | McClure | 606/224 |
| 1,960,117 | 5/1934 | Lydeard | 606/234 |
| 1,981,651 | 11/1934 | Logan | 606/224 |
| 2,022,234 | 11/1935 | Everett | 606/223 |
| 2,240,330 | 4/1941 | Flagg et al. | 606/224 |
| 2,302,986 | 11/1942 | Vollrath | 606/224 |
| 2,411,079 | 11/1946 | Baule | 606/224 |
| 2,802,468 | 8/1957 | Everett | 606/223 |
| 2,814,296 | 11/1957 | Everett | 606/223 |
| 2,910,983 | 11/1959 | Everett | 606/224 |
| 2,928,395 | 3/1960 | Forbes et al. | 606/224 |
| 3,311,110 | 3/1967 | Singerman et al. | 606/224 |
| 3,394,704 | 7/1968 | Dery | 606/224 |
| 3,416,534 | 12/1968 | Quinn | |
| 3,799,169 | 3/1974 | Beroff et al. | 606/227 |
| 3,835,912 | 9/1974 | Kristensen et al. | 606/224 |
| 3,875,946 | 4/1975 | Duncan | 606/227 |
| 3,877,570 | 4/1975 | Barry | 206/63.3 |
| 3,880,167 | 4/1975 | Hardwick | 606/227 |
| 3,890,975 | 6/1975 | McGregor | 606/227 |
| 3,910,282 | 10/1975 | Messer et al. | 606/225 |
| 3,918,455 | 11/1975 | Coplan | 606/227 |
| 3,924,630 | 12/1975 | Walldorf | 606/226 |
| 3,926,194 | 12/1975 | Greenberg et al. | 606/227 |
| 3,943,933 | 3/1976 | Gertzman | 606/227 |
| 3,949,756 | 4/1976 | Ace | 606/227 |
| 3,963,031 | 6/1976 | Hunter | 606/227 |
| 3,980,177 | 9/1976 | McGregor | 606/227 |
| 3,981,307 | 9/1976 | Borysko | 606/224 |
| 4,054,144 | 10/1977 | Hoffman et al. | 606/225 |
| 4,072,041 | 2/1978 | Hoffman et al. | 606/225 |
| 4,124,027 | 11/1978 | Boss | 606/225 |
| 4,127,133 | 11/1978 | Martinez | 606/224 |
| 4,169,477 | 10/1979 | Bokros | 29/447 |
| 4,359,053 | 11/1982 | Benjamin | 606/224 |
| 4,411,654 | 10/1983 | Boarini et al. | 604/163 |
| 4,596,728 | 6/1986 | Yang et al. | 428/36 |
| 4,624,879 | 11/1986 | Van Dijck et al. | 428/102 |
| 4,672,734 | 6/1987 | Kawada et al. | 606/224 |
| 4,792,336 | 12/1988 | Hlavacek et al. | 623/13 |
| 4,805,292 | 2/1989 | Noguchi | 606/224 |
| 4,926,860 | 5/1990 | Stice et al. | 606/144 |

FOREIGN PATENT DOCUMENTS

0358451  3/1990  European Pat. Off.
2432861  3/1980  France ................... 606/228

OTHER PUBLICATIONS

Raychem Corporation Product specification RT-850 for Thermofit™ Kynar Tubing dated Mar. 6, 1984

*Primary Examiner*—Stephen C. Pellegrino
*Assistant Examiner*—Gary Jackson
*Attorney, Agent, or Firm*—Thomas R. Bremer; Peter G. Dilwroth; Rocco S. Barrese

[57] ABSTRACT

A combined surgical needle-suture device of controlled suture release characteristics and a method for manufacturing the device employ a shrinkable tubing and a bonding agent to attach the needle to the suture.

37 Claims, 5 Drawing Sheets

SURGICAL NEEDLE-SUTURE ATTACHMENT FOR CONTROLLED SUTURE RELEASE

CROSS REFERENCE TO RELATED APPLICATIONS

This application is a continuation-in-part of commonly assigned, copending U.S. patent application Ser. No. 07/532,961 filed June 4, 1990 and now U.S. Pat. No. 5,067,959 which is a continuation-in-part of commonly assigned, copending U.S. patent application Ser. No. 07/413,240 filed Sept. 27, 1989 and now abandoned.

BACKGROUND OF THE INVENTION

The present invention relates to a method for attaching a surgical needle to a suture to provide a combined surgical needle-suture device possessing controlled suture release characteristics and, more particularly, to such a method in which a shrinkable tubing is employed to secure the needle to the suture.

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the *United States Pharmacopeia* (USP). The *United States Pharmacopeia* prescribes minimum individual pull-out forces and minimum average pull-out forces as measured for five needle-suture combinations. The minimum pull-out forces for both standard and removable needle-suture attachment set forth in the *United States Pharmacopeia* are hereby incorporated by reference.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out value of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g., by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 describes a needlesuture attachment wherein a hollow suture portion is secured to the shank end of a needle which is of reduced crosssection as compared to the remainder of the needle.

Additional patents which describe the use of tubing to effect suture-needle attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117, and 1,591,021.

Numerous disadvantages exist With methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle siliconization process. Safeguards employed in an attempt to prevent the introduction of such foreign materials, e.g., water blocking during needle silconization, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needlesuture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region. Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

Commonly assigned, U.S. Pat. application Ser. No. 07/413,240, filed Sept. 27, 1989, of which the present application is a continuation-in-part, described a combined surgical needle-suture device and surgical needle-suture attachment method which overcomes the aforementioned drawbacks of the previously known needle-suture combinations and needle-suture attachment methods. In accordance with said application, a combined surgical needle-suture device is provided in which a surgical needle having a shank of reduced cross-section is attached to a suture through a shrinkable tubing, or micro-ferrule, which is fitted about the needle shank and a portion of the suture. Application of energy to the shrinkable tubing brings the tubing into engagement with both the needle shank and the suture. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-suture combinations and removable needle-suture combinations using a single attachment process and a common inventory of materials.

Minimum average pull-out forces for various sizes of combined surgical needle-suture devices are set forth in the *United States Pharmacopeia* and are as follows:

TABLE 1

| Suture Size | Average Pull-Out Force/Ounces |
|---|---|
| 8/0 | 2.39 |
| 7/0 | 3.20 |
| 6/0 | 5.92 |
| 5/0 | 7.97 |
| 4/0 | 15.97 |
| 3/0 | 23.63 |
| 2/0 | 38.80 |
| 1/0 | 52.89 |
| 1 | 63.48 |
| 2 and larger | 63.48 |

U.S. Pat. No. 3,875,946, referred to supra, describes needle-suture combinations said to exhibit suture pull-out values that are substantially less than those given by the *United States Pharmacopeia* are set forth above. According to U.S. Pat. No. 3,875,946, employing the procedure described therein, combined surgical needle-suture devices can be obtained with the following average pull-out forces:

TABLE 2

| Suture Size | Average Pull-Out Force/Ounces |
|---|---|
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

These pull-out forces are obtained by prestressing the suture, i.e., by applying tension to the suture after the tip of the suture has been inserted into an axial bore, or recess, formed in the blunt end of the needle and the needled suture has been swaged so that the force required to pull the suture out of the recess exceeds the minimum limits on needle attachment set forth in the *United States Pharmacopeia* but is less than the actual tensile strength of the suture used. As the suture is pulled from the needle during application of the tensioning force, the force required to move the suture relative to the swaged section decreases. When the tensioning force required to move the end of the suture relative to the needle recess drops to the desired pull-out value, the tension is released.

The foregoing procedure is said to permit better control of the resulting needle-suture device in that the force required to separate a suture of a particular size from its attached needle is uniform.

In the approach to achieving controlled needle-suture separation described in aforementioned U.S. Pat. No. 4,127,133, the contents of which are incorporated by reference herein, a combined surgical needle-suture device of the drilled recess variety employs a bonding agent, specifically, a hot melt wax, to effect attachment of the suture to the needle. The bonding agent possesses a strength sufficient to secure the needle to the suture during surgery but which allows the needle to be deliberately separated from the suture by a sharp tug at the end of the surgical procedure. The bonding agent provides pull-out values ranging from 1–56 ounces depending on the size of the suture.

While the use of the tubing method disclosed in U.S. patent application Ser. No. 07/413,240 for needle-suture attachment has been found to be very effective, in the case of suture materials which are heat labile (i.e., those suture materials which tend to undergo some degree of degradation upon application of energy in the form of heat thereto) it is desirable to take precautions to treat a portion of the heat labile suture to prevent the suture material which is proximate to the energy and possibly exposed to such energy during the shrinkable tubing attachment process from undergoing a degradation of its physical qualities (i.e., tensile strength, etc.) or blemishing.

As used herein the term "heat labile material" refers to materials which may undergo physical, chemical and/or biological change or breakdown when exposed to energy. A heat labile suture is a suture fabricated from a material that is heat labile and undergoes some degree of breakdown of its components when exposed to sufficient energy, for example, heat energy. Most suture materials are sensitive to energy if exposed for an extended period of time; the list of heat labile suture materials affected by heat shrinking processes includes but is not limited to catgut, silk, nylon, polyester, polypropylene, linen, cotton, and/or absorbable synthetic materials for example, copolymers of glycolic and lactic acids.

Commonly assigned, copending U.S. Pat. application Ser. No. 07/661,693 filed Feb. 27, 1991 and now U.S. Pat. No. 5,102,418 issued Apr. 7, 1992 discloses and claims a method and apparatus for attaching a needle to a heat labile suture which involves desensitizing at least a tip portion of the heat labile suture. While the attachment technique of desensitizing the suture tip region has been found to be very effective in coupling a heat labile suture to a needle, it would be desirable to eliminate the need to treat or otherwise desensitize the tip region of the heat labile suture.

SUMMARY OF THE INVENTION

Accordingly, it is an object of the present invention to provide an improved method for attaching a shrinkable tubing to a needle and suture to provide a combined surgical needle-suture device.

An additional object of the present invention is to provide a needle-suture attachment means which eliminates the need for drilling a bore in the needle shank and swaging a suture therein.

It is also an object of the present invention to provide an attachment means which reliably secures the suture to the needle in an efficient manner, without close tolerances between elements.

It is another object of the present invention to provide a needle-suture attachment which is flexible and atraumatic.

It is a further object of the present invention is to provide needle-suture attachments having desired pull-out forces.

It is still a further object of the present invention to provide a shrinkable tubing attachment method for use with heat labile suture materials.

It is yet a further object of the present invention to eliminate need to desensitize or otherwise treat a tip region of a heat labile suture prior to coupling the same to a needle via a shrinkable tubing attachment.

In accordance with the present invention, there is provided a method for attaching a surgical needle to a suture to provide a combined surgical needle-suture device exhibiting a predetermined average range of needle separation force for a suture of given size which comprises:

a) providing a surgical needle possessing a shank end of reduced cross-section and a suture possessing a tip region for attachment to the reduced diameter shank end of the needle;

b) providing a shrinkable tubing for placement around the reduced diameter shank end of the needle and the tip region of the suture;

c) providing a bonding agent upon at least some portion of the inner surface of the shrinkable tubing to come into contact with the tip region of the suture and/or upon at least some portion of the tip region of the suture;

d) placing the shrinkable tubing around the reduced diameter shank end of the needle and the tip region of the suture;

e) applying energy to the shrinkable tubing to contract the tubing and bring it into engagement with the shank end of the needle and the tip region of the suture thereby resulting in attachment of the needle to the suture and providing the combined surgical needle-suture device, the combined attachment effect of the contracted tubing and the bonding agent being sufficient to provide a predetermined average range of needle separation force.

In addition to the foregoing surgical needle-suture attachment method, the present invention includes the resulting combined surgical needle-suture device.

The above-noted objects along with other objects are also accomplished by a method in accordance with the present invention for attaching a surgical needle to a suture to provide a combined surgical needle-suture device exhibiting a predetermined average range of needle separation force for a suture of given size which comprises:

a) providing a surgical needle possessing a shank end of reduced cross-section and a suture possessing a tip region for attachment to the reduced diameter shank end of the needle;

b) providing a shrinkable tubing for placement around the reduced diameter shank end of the needle and the tip region of the suture;

c) placing the shrinkable tubing around the reduced diameter shank end of the needle and around a gauging device;

d) applying energy to the shrinkable tubing to contract the tubing and bring it into contact with the shank end of the needle and the gauging device, whereby at least a portion of the tubing is shrunk to possess an inner opening substantially equal to the outer dimensions of the gauging device;

e) removing the gauging device from the tubing and leaving the tubing attached to the needle shank whereby the tubing possesses an open end having the opening of the dimensions substantially equal to the outer dimensions of the removed gauging device;

f) disposing a bonding agent upon at least some portion of the inner surface of the shrunken tubing through the open end thereof and/or upon at least some portion of the tip region of the suture; and, g) inserting the tip region of the suture into the open end of the shrunken tubing.

The bonding agent is then allowed to dry to provide attachment of the needle to the suture and thereby the combined surgical needle-suture device in which the suture is releasably retained in the tubing by the bonding agent, without any constriction of the tubing around the suture. The present invention is also directed to this resulting combined surgical needle-suture device.

BRIEF DESCRIPTION OF THE DRAWINGS

The present invention will become more apparent from the following detailed description taken in conjunction with the accompanying drawings in which.

DETAILED DESCRIPTION OF THE INVENTION

The present invention relates to a combined surgical needle-suture method and resulting surgical needle-suture device featuring controlled suture release. The invention has application to any suture material whether absorbable or non-absorbable, natural or synthetic, braided or monofilament, heat labile or non-heat labile and to any needle material and configuration whether straight or curved.

As used herein, the expressions "needle separation" and "suture release" are to be regarded as functionally equivalent since the effect of "needle separation" and "suture release" are one and the same, i.e., the needle and suture become detached from one another.

Figure 1:
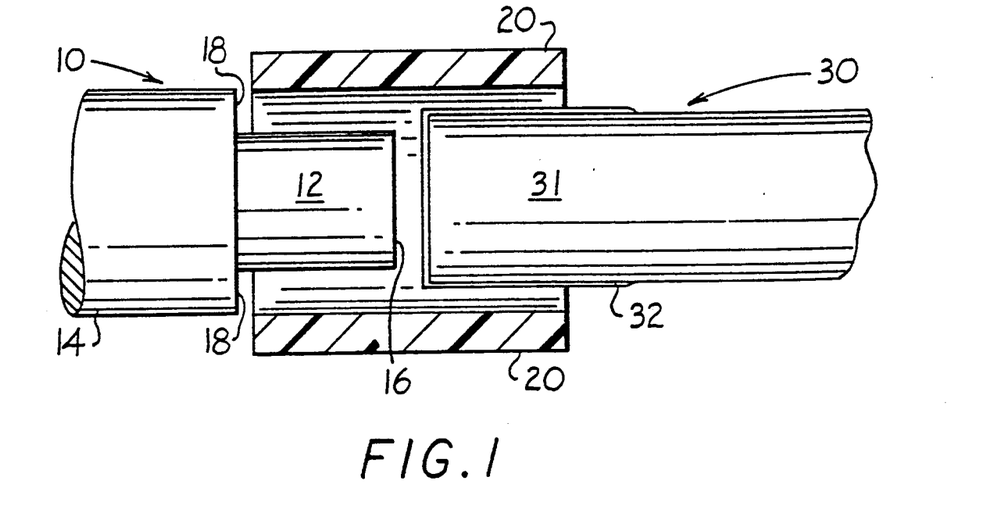
FIG. 1 is a side cross-sectional view of a surgical needle possessing a shank end of reduced diameter and a suture possessing a bonding agent-coated tip region with a shrinkable tubing positioned around the needle shank and suture tip (prior to engagement of the tubing with the needle and suture)
Figure 2:
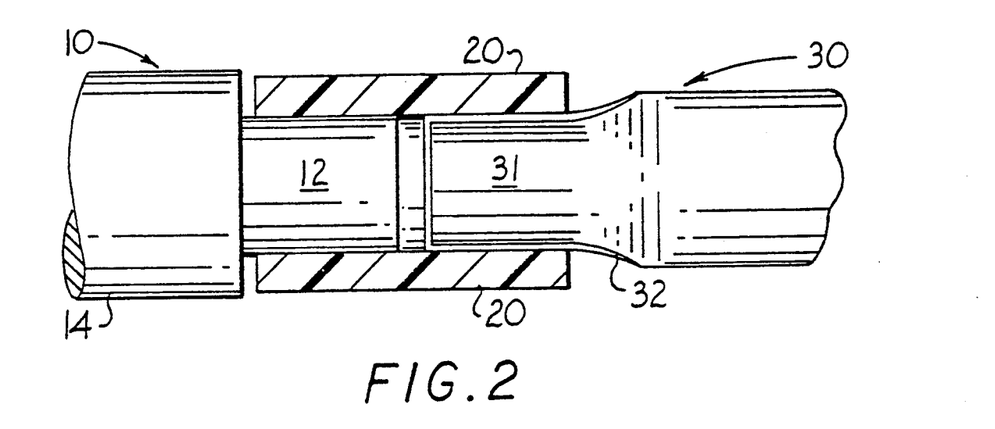
FIG. 2 is a side cross-sectional view of the needle and suture combination of FIG. 1 following shrinking of the tubing to effect engagement of the needle and suture.
Figure 3:
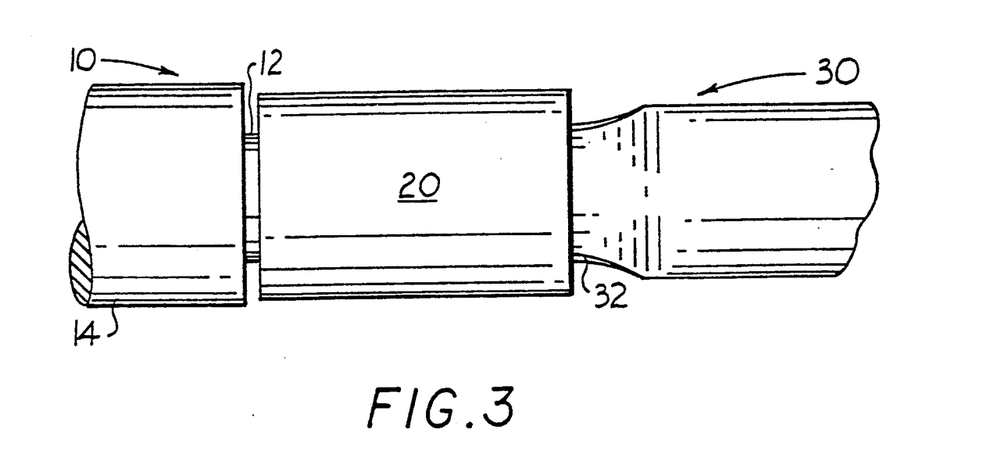
FIG. 3 is a side view of the combined surgical needle-suture device of FIG. 2.
Figure 4:
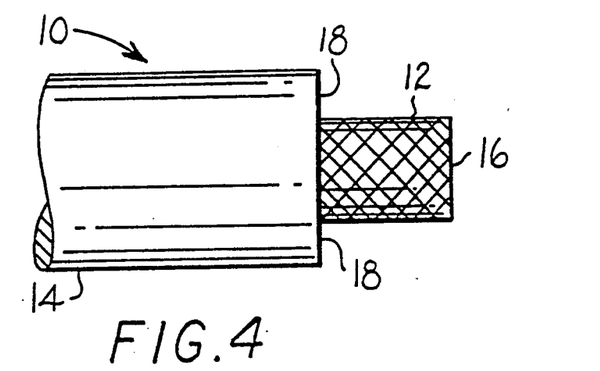
FIG. 4 is a side view of an alternative embodiment of the present invention in which the needle shank is scored.
Figure 5:
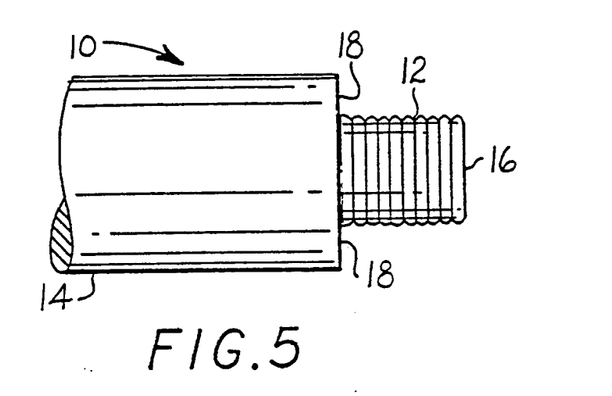
FIG. 5 is a side view of an alternative embodiment of the present invention in which the needle shank is ribbed.
Figure 6:
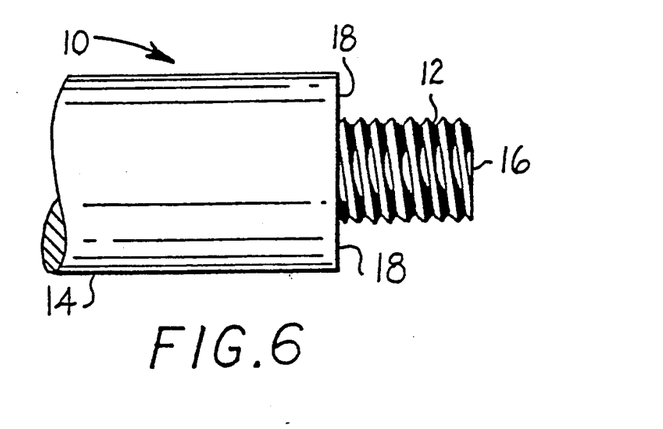
FIG. 6 is a side view of an alternative embodiment of the present invention in which the needle shank is threaded.
Figure 7:
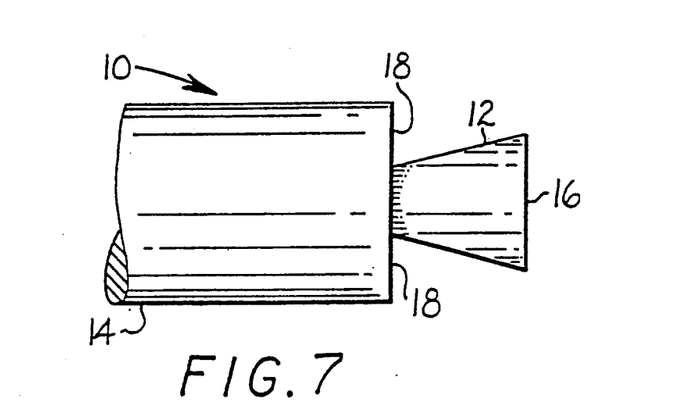
FIG. 7 is a side view of an alternative embodiment of the present invention in which the needle shank is tapered to expand in a direction away from a remainder of the needle.
Figure 8:
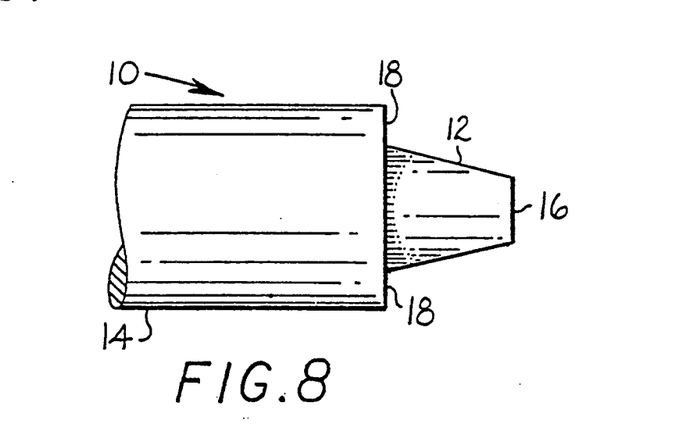
FIG. 8 is a side view of an alternative embodiment of the present invention in which the needle shank is tapered to expand in a direction towards the remainder of the needle.

Referring to FIGS. 1-3, needle 10 has a reduced cross-sectional diameter at its shank end 12 relative to the remainder of needle 14. The diameter of shank end 12 can be reduced by any conventional means, e.g., by machining on a lathe. Typically, shank end 12 has a diameter from 10 to 65% smaller than the remaining portion 14 of needle 10, and preferably from 25 to 50% smaller. It is also possible to provide shank end 12 with a texturized surface to facilitate gripping by shrinkable tubing 20. For example, shank end 12 can be scored, ribbed or threaded, in whole or in part (FIGS. 4-6 respectively). It can also be desirable to taper shank end 12 such that its butt, or distal, end 16 is of greater cross-sectional diameter than the cross-sectional diameter of shank end 12 in the region of shoulder 18, or vice versa (FIGS. 7 and 8 respectively).

Tip region 31 of suture 30 possesses a layer of bonding agent 32 on at least some portion of its surface. The combined action of tubing 20 following its contraction and bonding agent 32 functions to provide a separation force for separation of needle 14 from suture 30 to within a predetermined average range, e.g., from about 1-56 ounces depending on suture size, as in aforementioned U.S. Pat. No. 4,127,133. It is preferred that the average range of needle separation force fall within the following range of values for the size of suture indicated:

TABLE 3

| Suture Size | Average Needle Separation Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

Either or both suture tip region 31 and inner surface of shrinkable tubing 20 which is to make contact with suture tip region 31 can be provided with the bonding agent, e.g., as a layer or coating thereof on their respective surfaces. The same or different bonding agents can be used in coating the inner surface of the tubing and the tip of the suture where both are coated.

The bonding agents which are useful herein include any non-toxic adhesive composition which can be organic and/or inorganic. Suitable organic adhesives include natural materials such as starch, dextrins, asphalt, animal and vegetable proteins, natural rubber and shellac. Semisynthetic adhesives include cellulose nitrate, other cellulosics, polyamides derived from dimer acids, and castor-oil based polyurethanes. Synthetic adhesives include vinyl-type addition polymer resins such as polyvinyl acetate, polyvinyl alcohol, acrylics, unsaturated polyesters, butadiene/acrylonitrile, butadiene/styrene, neoprene, butyl rubber and polyisobutylene. Polymers formed by condensation or other step-wise mechanisms such as epoxies, polyurethanes, polysulfide rubbers, reaction products of formaldehyde and phenol, resorcinol, urea or melamine are also suitable synthetic adhesives.

More preferably, the bonding agent material includes epoxies and monomers or polymers of cyanoacrylate. Most preferably, the bonding agent is selected from the group of 2-cyanoacrylate ester polymers such as methyl 2-cyanoacrylate and ethyl 2-cyanoacrylate which possess excellent adhesive characteristics. Preparation and properties of these 2-cyanoacrylic ester adhesives are described, e.g., at Coover, Jr., et al., "2-Cyanoacrylic Ester Polymers", *Kirk-Othmer, Encyclopedia of Chemical Technology, Third Edition, Volume* 1, John Wiley & Sons (N.Y.), pages 408-413. The preferred cyanoacrylate is available under the name LOCTITE(TM) Medical Device Adhesive 18014 and is available from the Loctite Corporation, 705 N. Mountain Road, Newington, CT 06111. The preferred Loctite Medical Device Adhesive is a moisture activated polymer which comprises 99+% ethyl cyanoacrylate and small amounts of hydroquinone and organic anhydride. It has a specific gravity of 1.05 and a boiling point greater than 300° F.

The cyanoacrylate monomer may be applied in a variety of ways to the tubing and/or the suture. Upon contact with the suture, the residual moisture of the suture and surrounding environment catalyzes the polymerization of the cyanoacrylate almost instantly. The polymerized cyanoacrylate stiffens the segment of the suture by coating the individual filaments of the suture with a relatively stiff coating, and because the cyanoacrylate is an adhesive, the suture and tubing are retained together. A further advantage of ethyl cyanoacrylate is that it is bioabsorbable and will not leave a permanent residue in body tissue. Because the cyanoacrylate polymerizes almost instantly, the bonding agent is stiffened immediately without any additional drying or curing steps. This has the added advantage of reducing processing steps and accompanying handling and equipment requirements.

The bonding agent can be applied to the inner surface of shrinkable tubing 20 and or the surface of suture tip 31 by melt-dipping or as a solution in a suitable carrier or solvent, e.g., petroleum ether or other suitable hydrocarbon solvent in the case of the foregoing waxes. Other application methods include spraying, coating and so forth. The amount of bonding agent employed can vary over a relatively wide range and is not critical provided the resulting bond, or attachment, force in combination with the attachment force of tubing 20 following shrinking of the latter provide a predetermined needle separation force of appropriate magnitude, e.g., 1-56 ounces and preferably 1-26 ounces depending on the size of the suture. Specific quantities of bonding agent(s) for a particular combined surgical needle-suture device and desired pull-out force can be readily determined employing routine experimentation.

The material of suture 30 can be any of the filament-forming natural and synthetic materials heretofore employed in the fabrication of sutures, e.g., absorbable materials such as gut, collagen, homopolymers and copolymers of lactide and glycolide, etc., and non-absorbable materials such as silk, nylon, polypropylene, cotton, linen and some types of polyester.

Suture 30 is positioned within shrinkable tubing 20 with suture tip 31 abutting or separated a short distance from distal end 16 of shank 12. As shown in FIG. 1, suture 30 can initially be of uniform cross-section throughout its length. Alternatively, tip region 31 of suture 30, i.e., the region inserted into tubing 20, can be of reduced cross-section relative to the remainder of suture 30, e.g., by tipping the suture tip with an adhesive or resinous tipping agent while suture 30 is under tension. (See, e.g., Canadian Patent No. 1,009,532.) Resin tipping is advantageous in preventing brooming of the suture, particularly in the case of multifilament braided sutures, and/or to rigidify tip 31 to facilitate handling of the suture during attachment. Reducing the diameter of the suture tip, as by tipping under tension, may be desirable to allow a suture of larger diameter, e.g., a suture diameter equal to the diameter of the needle to which it is to be attached, to be more efficiently attached to the needle using the shrinkable tubing of the present invention. It is not necessary according to the present invention, however, to reduce the diameter of tip region 31 to efficiently attach needle 10 to suture 30. Indeed, it may be possible or desirable to apply a tipping agent to prevent brooming without reducing suture diameter. As shown in FIG. 1, shrinkable tubing 20 initially has an inner diameter that is larger than the outer diameter of suture tip region 31, thereby reducing the importance of suture tipping.

After shrinkable tubing 20 is placed around shank end 12 of needle 10 and tip region 31 of suture 30, energy is applied to tubing 20. In response to this energy, tubing 20 contracts or shrinks and engages shank end 12 and suture tip region 31. At the same time, this application of heat melts a wax bonding agent 32 such that on re-solidification of the wax, the subsequent adhesive bond formed between suture tip 31 and the inner wall of constricted tubing 20 and the gripping force of tubing 20 effect attachment of the needle and suture. Suitable energy sources include heat (convective or conductive), radiation, microwave energy, etc.

As shown in FIGS. 1-2, shrinkable tubing 20 is simultaneously placed around both suture tip region 31 and shank end 12 of needle 10 in one embodiment of the present invention. It is preferable, however, to sequentially secure tubing 20 to needle 10 and suture tip region 31. Thus, in a preferred embodiment of the present invention, shrinkable tubing 20 is initially secured to shank end 12 through the localized application of energy to tubing 20 in the region surrounding shank end 12. After tubing 20 has been brought into engagement with shank end 12, tip 31 of suture 30 is inserted into tubing 20 and additional energy is applied thereto. Sequential shrinkage of tubing 20 makes it possible to vary the amount of energy used in securing tubing 20 to shank end 12 and suture tip 3!, respectively, and to limit the exposure of suture 30 to energy during the attachment process. It may also be desirable to cool suture 30 in the region outside tubing 20 to prevent any undesirable degradation thereof, e.g., with a cold air curtain.

As shown in FIG. 2, the shrinkage of tubing 20 typically compresses suture 30 to some extent. This is particularly true where the suture is a braided multi-filament material having void spaces in its structure. For example, tubing 20 may compress suture 30 by as much as 30 to 35% for a braided, synthetic absorbable suture and by a minimal amount for a relatively stiff material such as a monofilament surgical gut.

Shrinkable tubing 20 can be manufactured from any material which shrinks, i.e., reduces in diameter, in response to the application of energy. Suitable materials include "memory metals," e.g., nickel-titanium mixtures, nickel-iron-titanium mixtures, or copper based materials, as are well known in the art (see, e.g., U.S. Pat. Nos. 3,759,552, 3,801,954, 4,198,081, and 4,773,680), and shrinkable plastic materials such as polyvinylidene fluoride materials available from Raychem Corporation, Menlo Park, Calif. under the tradename Kynar. In the case of shrinkable plastic materials, the tubing is typically extruded such that the inner diameter is less than the final desired inner diameter, i.e., the inner diameter of the tubing after energy application in the attachment method of the present invention. Thereafter, the extruded tubing is expanded radially outward through radial expansion means to provide a tubing of expanded inner diameter as shown, for example, by tubing 20 in FIG. 1. Such plastic tubing is thus adapted to shrink, or "recover", to its original extruded inner diameter in response to the application of a predetermined amount of energy.

The amount of energy applied to tubing 20 to effect the desired attachment, i.e., diameter reduction, depends upon the chemical characteristics of the tubing material, the relative dimensions of the tubing, the shank end of the needle and the suture, and the desired pull-out force for the needle-suture combination. For example, one polyvinylidene fluoride material available from Raychem Corporation (RT-850) shrinks at temperatures greater than 175° C., and is adapted to recover to about 50% of its radially expanded inner diameter. In such case, tubing 20 may be brought into engagement with shank end 12 of needle 10 and suture tip region 31, either simultaneously or sequentially, by heating tubing 20 to a temperature above 175° C. Tubing 20 may be heated through contact with a hot gas stream or with heated dies, or by other heating means. Typically, the outer diameters of shank end 12 and suture tip region 31 are greater than the fully recovered diameter of tubing 20, e.g., greater than 50% of the initial inner diameter of tubing 20 for the RT-850 material, such that tubing 20 engages shank end 12 and suture tip region 31. It is preferred that the attachment conditions be controlled such that the tubing remains secured to the needle once the suture is detached.

Figure 9:
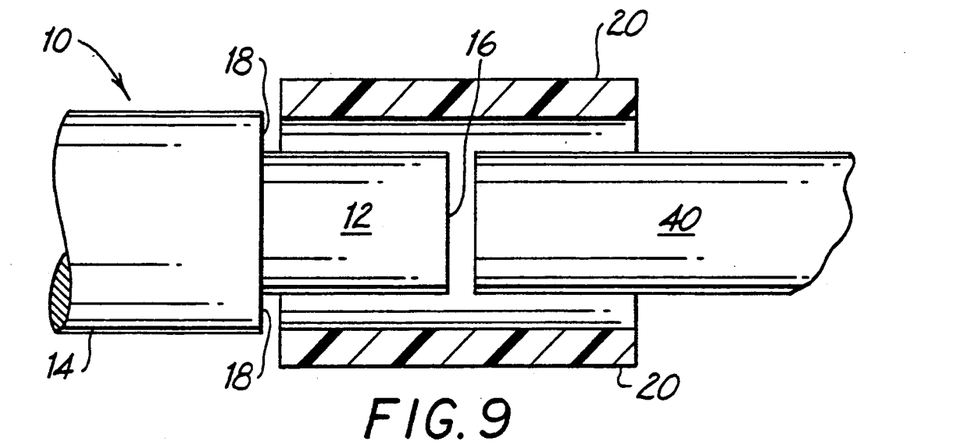
FIG. 9 is a side cross-sectional view of a surgical needle possessing a shank end of reduced diameter, a gauging device of predetermined outer dimensions, with a shrinkable tubing positioned around the needle shank and gauging device (prior to engagement of the tubing with the needle and gauging device)
Figure 10:
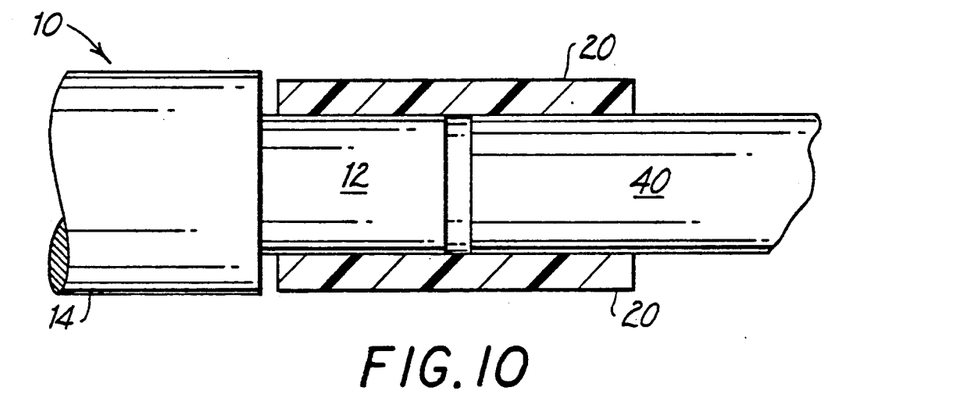
FIG. 10 is a side cross-sectional view of the needle and gauging device combination of FIG. 9 following shrinking of the tubing to effect engagement of the needle and gauging device.
Figure 11:
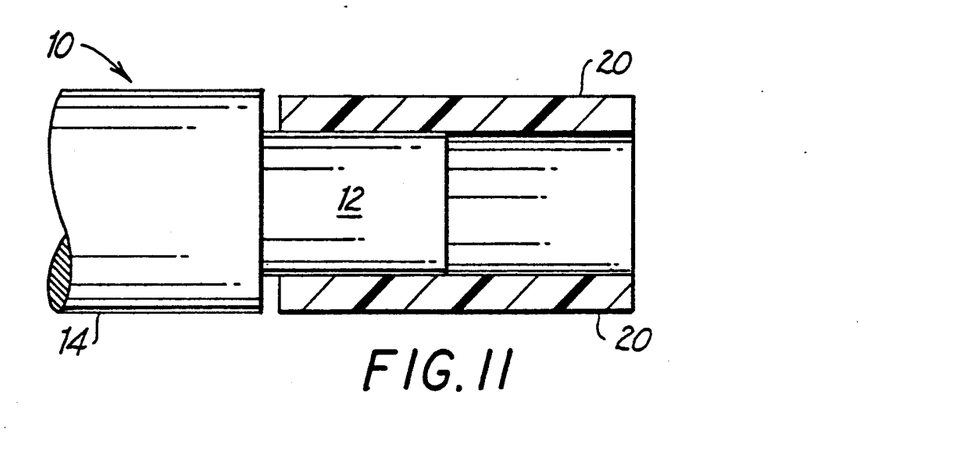
FIG. 11 is a side cross-sectional view similar to FIG. 10 and after removal of the gauging device from an end of the shrunken tubing.
Figure 12:
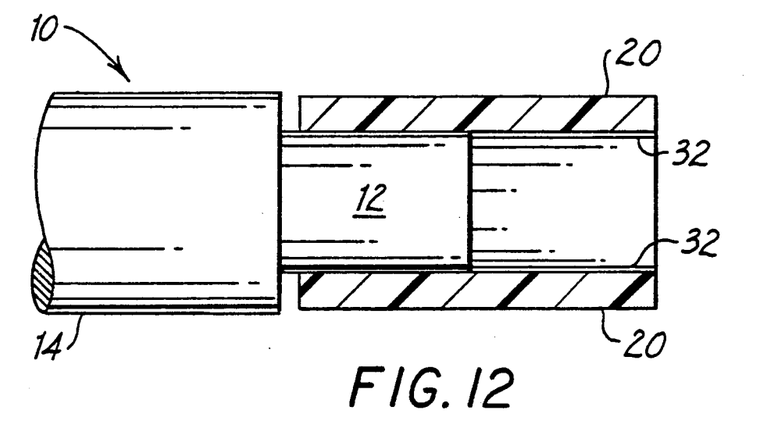
FIG. 12 is a side cross-sectional view similar to FIG. 11 and after application of bonding agent to an internal surface of the tubing.
Figure 13:
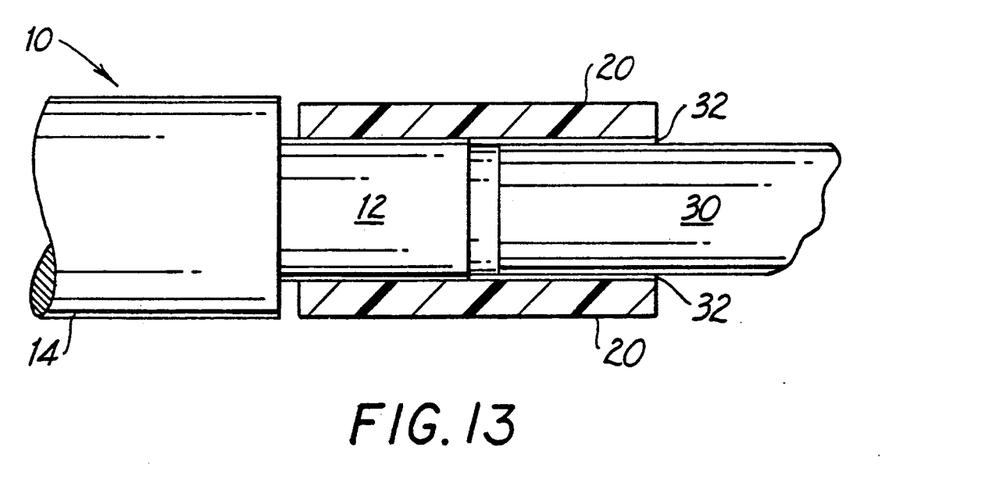
FIG. 13 is a side cross-sectional view similar to FIG. 12 after a tip of the suture has been inserted into an end of the shrunken tubing.

Referring to FIGS. 9-13, the tubing can be placed around the shank end 12 of the needle 10 and also around a gauging device, e.g., a gauge pin 40 of predetermined outer dimension or diameter (FIG. 9). Energy is then applied to the tubing 20 which contracts or shrinks and engages both shank end 12 and gauge pin 40 as shown in FIG. 10. Then, gauge pin 40 is removed from within the tubing 20, leaving just the needle 10 coupled to the tubing 20 at shank end 12 as illustrated in FIG. 11. At this point, the bonding agent 32 is applied to the inner surface of the shrunken tubing 20, i.e., the area of the tubing 20 from which the gauge pin 40 was removed as illustrated in FIG. 12. The suture 30 is then inserted into the open end of the shrunken tubing 20 to make contact with the inner surface thereof and bonding agent 32. The bonding agent 32 is then allowed to dry or harden to form the combined surgical needle-suture device illustrated in FIG. 13 in which the suture 30 is releasably retained in the tubing 30 by the bonding agent 32 and not by any constriction of the tubing 20 around the suture 30.

While FIG. 12 illustrates the bonding agent 32 as being applied to the inner surface of the tubing 20 before introduction of the suture 30, the bonding agent 32 can be applied to the tip region of the suture 30 instead of upon the inner surface of the tubing 20. Furthermore, the bonding agent 32 can be applied onto both the inner surface of the tubing 20 and onto the tip region of the suture 30. The suture 30 itself can also be provided with resinous tipping agent in the manner described supra to prevent brooming.

The procedure illustrated in FIGS. 9-13 is especially suited for providing removable needle-suture combinations of heat-sensitive or heat labile sutures, e.g., those sutures made of material which tends to undergo some degree of degradation upon application of energy in the form of heat thereto.

The tubing 20 in the embodiment illustrated in FIGS. 9-13 can be manufactured from any of the materials enumerated supra which are shrinkable in response to application of energy. Preferably, the tubing 20 is manufactured from polyethylene because this material has a greater maximum shrinkage at a lower temperature than other possible materials and is also resistant to packing fluid for the suture, such as isopropyl alcohol used for packing catgut sutures. The tubing 20 preferably has a minimum expanded diameter of 0.027 inches for catgut suture sizes 2/0, 0 and 1 and 0.018 inches for catgut suture sizes 3/0 and 4/0.

The gauge pin 40 is manufactured from material which is not heat shrinkable so that dimensions of the pin are maintained upon shrinking of the tubing 20 to define the opening in the tubing 20 for ultimately receiving the suture 30. In this regard, the pin 40 can be prepared from material such as hardened stainless steel. A preferred material is bearing steel hardened to 60-62 Rockwell. Additionally, the surface of the gauge pin 40 is preferably polished so that the pin 40 and shrunken tubing 20 will not adhere to one another. The preferred surface finish is 10 microns or better. The gauge pin is preferably in the shape of a cylinder having a diameter for each suture size as follows:

TABLE 4

| SUTURE SIZE | GAUGE PIN DIAMETER (INCHES) |
| --- | --- |
| 1 | 0.0245 |
| 0 | 0.020 |
| 2/0 | 0.018 |
| 3/0 | 0.013 |
| 4/0 | 0.011 |

The foregoing surgical needle-suture attachment procedure has many advantages over previous attachment methods. Machining of the needle to provide a reduced diameter needle shank is much easier and more controllable than drilling processes, and permits the use of needle alloys which have previously been impractical, e.g., Series 300 stainless steel and MP35N (available from SPS Technologies). These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply. The tubing used in the present invention may be color coded to designate suture material, standard versus detachable attachment, etc., particularly where a plastic tubing is employed.

The attachment method is also much more efficient from a processing and inventory control standpoint. For example, the tubing may be removed from a needle and the needle attached to a fresh suture, e.g., in instances where the suture and/or attachment properties of the initial suture-needle combination are outside specifications. In many instances, the suture may also be recovered and reused, thereby greatly reducing processing waste. The range of acceptable suture diameters is greatly expanded due to the ability of the tubing to recover or shrink to varying degrees, thereby minimizing the likelihood that suture production will be rejected for inability to attach several needle sizes. This greatly simplifies inventory considerations. Moreover, the needle-suture combinations are atraumatic and advantageously exhibit flexibility in the attachment region.

In this regard, it has been found that a detachable suture-needle combination can be provided which exhibits more consistent detachment (pull-out) force than known types of detachable needle-suture combinations of comparable size. More specifically, it has been found that a removal interface characterized by optimized suture tip surface characteristics in combination with optimized shrinkable tubing suture contact area results in a detachable suture-needle combination with a more consistent detachment force than the known types of standard detachable suture-needle combinations.

As used herein, the expression "standard detachable needle-suture" refers to a detachable needle-suture combination in which the force to separate the needle from the suture is within the range of pull-out forces set forth in the United States Pharmacopeia for removable needle-suture combinations, and includes detachable or removable needle-suture combinations commercially available from Ethicon, Inc. (Johnson & Johnson) and Davis & Geck (American Cyanamid Co.)

The present invention now makes it possible to provide a detachable needle-suture combination having a detachment force which is more consistent than the detachment force of standard detachable needle-suture combinations. When the suture-needle device is to be of the detachable variety, the ratio of the axial length of the tubing 20 to the effective axial length of the needle shank 12 must not exceed about 3.5:1, and preferably should not exceed about 3.2:1. For practical considerations, it is preferable that this ratio not be less than about 1.2:1 and more preferably not less than about 1.4:1. To accomplish this highly desirable result, it has been found that the parameters set out in the Table 5 below are preferred.

In Table 5, specific ratios of the axial length of the tubing 20 (ALT) to the effective axial length of the needle shank 12 (EALS) are given for a variety of detachable combined surgical needle-suture devices manufactured from two types of heat labile sutures and needles. In this and the following tables, the designation of the suture type carries the following meaning:
PPM polypropylene monofilament
SGC chromic gut

TABLE 5

| | | DETACHABLE NEEDLE-SUTURE COMBINATIONS | | | | |
|---|---|---|---|---|---|---|
| Suture Type | Suture Size | Needle Diameter/ Inch | Shank Diameter/ Inch | EALS/ Inch | ALT/ Inch | Ratio Of ALT To EALS |
| SGC | 0 | 0.044 | 0.016 | 0.065 | 0.095-0.175 | 1.5:1-2.7:1 |
| SGC | 1 | 0.044 | 0.020 | 0.070 | 0.095-0.175 | 1.4:1-2.5:1 |
| SGC | 1 | 0.039 | 0.020 | 0.070 | 0.095-0.175 | 1.4:1-2.5:1 |
| PPM | 2/0 | 0.039 | 0.016 | 0.065 | 0.095-0.175 | 1.5:1-2.7:1 |
| PPM | 0 | 0.039 | 0.016 | 0.065 | 0.095-0.175 | 1.5:1-2.7:1 |
| SGC | 0 | 0.039 | 0.016 | 0.065 | 0.095-0.175 | 1.5:1-2.7:1 |
| PPM | 0 | 0.050 | 0.016 | 0.065 | 0.095-0.175 | 1.5:1-2.7:1 |
| PPM | 0 | 0.039 | 0.016 | 0.065 | 0.095-0.175 | 1.5:1-2.7:1 |
| PPM | 2/0 | 0.039 | 0.016 | 0.065 | 0.095-0.175 | 1.5:1-2.7:1 |
| PPM | 0 | 0.044 | 0.016 | 0.065 | 0.095-0.175 | 1.5:1-2.7:1 |
| PPM | 2/0 | 0.044 | 0.016 | 0.065 | 0.095-0.175 | 1.5:1-2.7:1 |
| SGC | 2/0 | 0.050 | 0.016 | 0.070 | 0.095-0.175 | 1.4:1-2.5:1 |
| SGC | 0 | 0.050 | 0.016 | 0.070 | 0.095-0.175 | 1.4:1-2.5:1 |
| PPM | 0 | 0.050 | 0.016 | 0.065 | 0.095-0.175 | 1.5:1-2.7:1 |
| SGC | 0 | 0.050 | 0.016 | 0.065 | 0.095-0.175 | 1.5:1-2.7:1 |
| PPM | 2/0 | 0.050 | 0.016 | 0.065 | 0.095-0.175 | 1.5:1-2.7:1 |
| PPM | 0 | 0.050 | 0.016 | 0.065 | 0.095-0.175 | 1.5:1-2.7:1 |

The parameters presented in Table 6 below are most preferred for providing a detachable needle-suture having a detachment force which is more consistent than the detachment force of standard detachable needle-suture combinations. In Table 6 below, the optimized contact areas between the shrinkable tubing 20 and the needle 10 and suture 30 are set forth as a function of tube 20, needle shank 12 and suture tip diameters and length. In addition, specific ratios of the approximate axial length of the tubing (ALT) to the approximate effective axial length of the shank (EALS) and to the approximate effective axial length of the suture tip (EALT) are set forth.

The areas, lengths, diameters and ratios set forth in Table 6 below relate to tube lengths and ratios prior to shrinking of the tube. The optimized suture contact area has been estimated by calculating the approximate surface area of the suture tip before being placed within the tube after shrinking the tube. The calculated area is believed to provide a reasonable indication of the attached structure. Furthermore, the axial length, and consequently the contact area, of the tube may alter somewhat, e.g. decrease, during shrinking, but it is desirable to minimize changes in the axial length of the tubing during shrinking and maximize recovery of the tube in the radial direction so as to provide a relatively constant tube length and contact area.

Indeed, in the context of detachable needles having more consistent pull-out force, it is important to provide a relatively constant contact area between the inner surface of the tubing 20 and the surface to be released from the tubing 20 upon application of a predetermined pull-out force. In addition, in the context of removable needles, it is desirable to have the tubing 20 remain attached to the needle shank 12, with detachment occurring at the interface of the tubing 20 with the suture tip. The parameters set forth in Table 6 below provide a removable needle-suture combination wherein detachment occurs between the tubing 20 and the suture 30 under application of a consistently reliable pull-out force.

TABLE 6

| Suture Type | Suture Size | Needle Diameter/ Inch | Shank Diameter/ Inch | EALS/ Inch | ALT/ Inch | Ratio of ALT to EALS | Ratio of ALT to EALT | Average Suture Tip Diam. (Inch) | Approximate Suture Tip/ Tube Contact Area (In²) |
|---|---|---|---|---|---|---|---|---|---|
| SGC | 0 | 0.044 | 0.016 | 0.065 | 0.115 | 1.77 | 2.30 | 0.016 | 0.0025 |
| SGC | 1 | 0.044 | 0.020 | 0.070 | 0.115 | 1.64 | 2.56 | 0.019 | 0.0027 |
| SGC | 1 | 0.039 | 0.020 | 0.070 | 0.115 | 1.64 | 2.56 | 0.019 | 0.0027 |
| PPM | 2/0 | 0.039 | 0.016 | 0.065 | 0.125 | 1.92 | 2.08 | 0.013 | 0.0025 |
| PPM | 0 | 0.039 | 0.016 | 0.065 | 0.125 | 1.92 | 2.08 | 0.015 | 0.0028 |
| SGC | 0 | 0.039 | 0.016 | 0.065 | 0.115 | 1.77 | 2.30 | 0.016 | 0.0025 |
| PPM | 0 | 0.050 | 0.016 | 0.065 | 0.125 | 1.92 | 2.08 | 0.015 | 0.0028 |
| PPM | 0 | 0.039 | 0.016 | 0.065 | 0.125 | 1.92 | 2.08 | 0.015 | 0.0028 |
| PPM | 2/0 | 0.039 | 0.016 | 0.065 | 0.125 | 1.92 | 2.08 | 0.013 | 0.0025 |
| PPM | 0 | 0.044 | 0.016 | 0.065 | 0.125 | 1.92 | 2.08 | 0.015 | 0.0028 |
| PPM | 2/0 | 0.044 | 0.016 | 0.065 | 0.125 | 1.92 | 2.08 | 0.013 | 0.0025 |
| SGC | 2/0 | 0.050 | 0.016 | 0.070 | 0.115 | 1.64 | 2.56 | 0.014 | 0.0020 |
| SGC | 0 | 0.050 | 0.016 | 0.070 | 0.115 | 1.64 | 2.56 | 0.016 | 0.0023 |
| PPM | 0 | 0.050 | 0.016 | 0.065 | 0.125 | 1.92 | 2.08 | 0.015 | 0.0028 |
| SGC | 0 | 0.050 | 0.016 | 0.065 | 0.115 | 1.77 | 2.30 | 0.016 | 0.0025 |
| PPM | 2/0 | 0.050 | 0.016 | 0.065 | 0.125 | 1.92 | 2.08 | 0.013 | 0.0025 |
| PPM | 0 | 0.050 | 0.016 | 0.065 | 0.125 | 1.92 | 2.08 | 0.015 | 0.0028 |

In the preferred detachable needle-suture configurations of Table 6 above, three different tubings were used whose additional dimensional characteristics are set forth in Table 7 below as follows:

TABLE 7
ADDITIONAL DIMENSIONAL CHARACTERISTICS OF THE TUBING EMPLOYED IN THE PREFERRED DETACHABLE NEEDLE-SUTURE COMBINATION OF TABLE 6

| Tubing | Suture Size | Shank Diameter/ Inch | Tubing Dimensions | | |
|---|---|---|---|---|---|
| | | | Minimum Expanded Inner Diameter/ Inch | Maximum Recovered Inner Diameter/ Inch | Maximum Recovered Wall Thickness/ Inch |
| 1 | 3/0, 4/0 | .010 | .014 | .007 | .0055 |
| 2 | 0, 2/0 | .016 | .018 | .012 | .0065 |
| 3 | 1 | .020 | .025 | .016 | .009 |

The lengths of the tubings are preferably to within about ±0.015 inch, more preferably to within about ± 0.010 inch and most preferably to within about ±0.005 inch. In order to accommodate small changes in braid diameter of a braided suture, it is contemplated that the tube could be as long as about 0.140 inch and possibly as long as about 0.155 to about 0.160 inch. Based on the pre-attachment length of the preferred tubing, the effective axial length of the needle shank and the average tip diameter of the various types and sizes of suture, it can be seen that the contact area between the effective axial length of the suture tip and the tubing will range from about 0.001 square inches to about 0.008 square inches, and that the axial length of the contact area ranges from about 0.045 inches to about 0.105 inches.

Broad and preferred tube to suture contact areas for each size suture are summarized in the Table 8 below.

TABLE 8
REMOVAL INTERFACE CONTACT AREA BY SUTURE SIZE (Part 1-Broad)

| Suture Size | Broad Suture Tip Diameter (In.) | Broad Tube Contact Length (In.) | Broad Contact Area (In²) |
|---|---|---|---|
| 1 | .016 to .024 | .045 to .105 | .0023 to .0079 |
| 0 | .014 to .020 | .045 to .105 | .0020 to .0066 |
| 2/0 | .012 to .017 | .045 to .105 | .0017 to .0053 |
| 3/0 | .008 to .013 | .045 to .105 | .0011 to .0043 |
| 4/0 | .006 to .010 | .045 to .105 | .0008 to .0033 |

(Part 2-Preferred)

| Suture Size | Preferred Suture Tip Diameter (In.) | Preferred Tube Contact Length (In.) | Preferred Contact Area (In²) |
|---|---|---|---|
| 1 | .018 to .022 | .060 to .090 | .0034 to .0062 |
| 0 | .015 to .019 | .060 to .090 | .0028 to .0054 |
| 2/0 | .012 to .016 | .060 to .090 | .0023 to .0048 |
| 3/0 | .010 to .012 | .060 to .090 | .0019 to .0034 |
| 4/0 | .008 to .010 | .060 to .090 | .0015 to .0028 |

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for attaching a surgical needle to a suture to provide a combined surgical needle-suture device exhibiting a predetermined average range of needle separation force for a suture of given size which comprises:
   a) providing a surgical needle possessing a shank end of reduced cross-section and a suture possessing a tip region for attachment to the reduced diameter shank end of the needle;
   b) providing a shrinkable tubing for placement around the reduced diameter shank end of the needle and the tip region of the suture;

c) placing the shrinkable tubing around the reduced diameter shank end of the needle and around a gauging device;

d) applying energy to the shrinkable tubing to contract the tubing and bring it into contact with the shank end of the needle and the gauging device, whereby at least a portion of the tubing is shrunk to possess an inner opening substantially equal to the outer dimensions of the gauging device;

e) removing the gauging device from the tubing and leaving the tubing attached to the needle shank whereby the tubing possesses an open end having the opening of dimensions substantially equal to the outer dimensions of the removed gauging device;

f) disposing a bonding agent upon at least some portion of the inner surface of the shrunken tubing through the open end thereof and/or upon at least some portion of the tip region of the suture; and, g) inserting the tip region of the suture into the open end of the shrunken tubing, the combined attachment effect of the shrunken tubing and bonding agent being sufficient to provide a predetermined average range of needle separation force.

2. The method of claim 1 wherein the suture is releasably retained in the shrunken tubing by the bonding agent, without any constriction of the tubing around the suture.

3. The method of claim 1 comprising the additional step of h) allowing the bonding agent to dry.

4. The method of claim 1 wherein the average needle separation force ranges from about 1 to 56 ounces.

5. The method of claim 1 Wherein the average needle separation force is within the following range for the stated size of suture:

| Suture Size | Average Pull-Out Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

6. The method of claim 1 wherein the bonding agent is selected from epoxies and monomers or polymers of cyanoacrylate.

7. The method of claim 6 wherein the bonding agent is selected from 2-cyanoacrylic ester polymers.

8. The method of claim 7 wherein the bonding agent is methyl 2-cyanoacrylate or ethyl 2-cyanoacrylate.

9. The method of claim 1 wherein the suture is a monofilament suture.

10. The method of claim 1 wherein the suture is a multifilament suture.

11. The method of claim 1 wherein the suture is fabricated from an absorbable or non-absorbable material.

12. The method of claim 11 wherein the suture is fabricated from heat labile material.

13. The method of claim 12 wherein the heat labile material is polypropylene, catgut or a copolymer of glycolic and lactic acid.

14. The method of claim 12 wherein said attachment is accomplished without desensitizing said heat labile material.

15. The method of claim 1 wherein the shrinkable tubing is fabricated from a shrinkable plastic.

16. The method of claim 15 wherein the shrinkable tubing is fabricated from a polyethylene polymer.

17. A combined surgical needle-suture device exhibiting a predetermined average range of needle separation force for a suture of given size which comprises:

a) a surgical needle possessing a shank end of reduced cross-section;

b) a suture possessing a tip region for attachment to the shank end of the needle;

c) a constricted tubing around the reduced diameter shank end of the needle and the tip region of the suture, the constricted tubing exerting an attachment force against the surface of the reduced diameter shank end of the needle with which the inner surface of the constricted tubing is in contact without swaging or crimping; and, d) a bonding agent upon at least some portion of the inner surface of the constricted tubing which is in contact with the tip region of the suture and/or upon at least some portion of the tip region of the suture in contact with the inner surface of the constricted tubing, the bonding force of the bonding agent providing a predetermined average range of needle separation force.

18. The combined surgical needle-suture device of claim 17 wherein the suture is releasably retained within the constricted tubing by the bonding agent without any constriction of the tubing around the suture.

19. The combined surgical needle-suture device of claim 17 wherein the average needle separation force ranges from about 1 to 56 ounces.

20. The combined surgical needle-suture device of claim 17 wherein the average needle separation force is within the following range for the stated size of suture:

| Suture Size | Average Pull-Out Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

21. The combined surgical needle-suture device of claim 17 wherein the bonding agent is selected from epoxies and monomers or polymers of cyanoacrylite.

22. The combined surgical needle-suture device of claim 21 wherein the bonding agent is selected from 2-cyanoacrylic ester polymers.

23. The combined surgical needle-suture device of claim 22 wherein the bonding agent is methyl 2-cyanoacrylate or ethyl 2-cyanoacrylate.

24. The combined surgical needle-suture device of claim 17 wherein the suture is a monofilament suture.

25. The combined surgical needle-suture device of claim 17 wherein the suture is a multifilament suture.

26. The combined surgical needle-suture device of claim 17 wherein the suture is fabricated from an absorbable or non-absorbable material.

27. The combined surgical needle-suture device of claim 26 wherein the suture is fabricated from heat labile material.

28. The combined surgical needle-suture device of claim 27 wherein the heat labile material is polypropylene, catgut or a copolymer of glycolic and lactic acid.

29. The combined surgical needle-suture device of claim 27 wherein said heat labile material is not desensitized.

30. The combined surgical needle-suture device of claim 17 wherein the shrinkable tubing is fabricated from a shrinkable plastic.

31. The combined surgical needle-suture device of claim 29 wherein the shrinkable tubing is fabricated from a polyethylene polymer.

32. The combined surgical needle-suture device of claim 17 wherein the shank end of the needle is provided with a texturized surface to facilitate gripping by said tubing.

33. The combined surgical needle-suture device of claim 32 wherein the shank end is scored, ribbed or threaded in whole or in part.

34. The combined surgical needle-suture device of claim 17 wherein the shank end of reduced cross-section forms a shoulder with a remainder of said needle.

35. The combined surgical needle-suture device of claim 34 wherein the shank end is tapered in a direction toward said shoulder, such that a distal end of said shank end is of greater cross-sectional diameter than cross-sectional diameter of said shank end in a region of said shoulder.

36. The combined surgical needle-suture device of claim 34 wherein said shank end is tapered in a direction away from said shoulder, such that a distal end of said shank end is of smaller cross-sectional diameter than cross-sectional diameter of said shank end in a region of said shoulder.

37. The combined needle-suture device of claim 17 wherein the needle is intended to be detached from the suture.

* * * * *